US008181643B2

(12) United States Patent
Friedberg

(10) Patent No.: US 8,181,643 B2
(45) Date of Patent: May 22, 2012

(54) SYSTEM AND METHOD FOR DETECTION AND REPAIR OF PULMONARY AIR LEAKS

(76) Inventor: Joseph S. Friedberg, Philadelphia, PA (US)

( * ) Notice: Subject to any disclaimer, the term of this patent is extended or adjusted under 35 U.S.C. 154(b) by 1323 days.

(21) Appl. No.: 11/738,106

(22) Filed: Apr. 20, 2007

(65) Prior Publication Data

US 2007/0251532 A1    Nov. 1, 2007

(51) Int. Cl.
*A61M 11/00* (2006.01)
*A61M 37/00* (2006.01)
(52) U.S. Cl. ............ 128/200.21; 604/24; 606/215
(58) Field of Classification Search .......... 128/200.21, 128/898; 604/23–26; 606/213–216
See application file for complete search history.

(56) References Cited

U.S. PATENT DOCUMENTS

| 2004/0236371 | A1* | 11/2004 | McNally-Heintzelman et al. ............ 606/213 |
| 2005/0281740 | A1* | 12/2005 | Gong et al. ............ 424/1.69 |
| 2006/0004400 | A1* | 1/2006 | McGurk et al. ............ 606/192 |
| 2006/0118125 | A1* | 6/2006 | Tanaka ............ 128/898 |
| 2007/0012724 | A1* | 1/2007 | Feinberg et al. ............ 222/137 |
| 2010/0291058 | A1* | 11/2010 | Bowlin et al. ............ 424/94.5 |

OTHER PUBLICATIONS

Otani, Yuto et al., "Sealing Effects of Rapidly Curable Gelatin—Poly (L-Glutamic Acid) Hydrogel Glue on Lung Air Leak", 1999 by The Society of Thoracic Surgeons, Published by Elsevier Science, Inc, pp. 922-926.*
Yuto Otani et al., "Effect of additives on gelation and tissue adhesion of gelatin-poly(L-glutamic acid) mixture", Biomaterials 19 (1998), pp. 2167-2173, Published by Elsevier Science Ltd.

* cited by examiner

*Primary Examiner* — Justine Yu
*Assistant Examiner* — Valerie L Skorupa
(74) *Attorney, Agent, or Firm* — Caesar, Rivise, Bernstein, Cohen & Pokotilow, Ltd.

(57) ABSTRACT

A method for repairing pulmonary air leaks in a lung residing in a chest cavity and having an intake air stream and an outer surface is disclosed. An exemplary method comprises: introducing a first component of a biphasic sealant component as a liquid into the intake air stream of the damaged lung; ensuring that there is a pressure differential between the intake air stream and the outer surface of the lung; and introducing a second component of a biphasic sealant component into the chest cavity. The first sealant component collects at the air leak site and forms a sealant in combination with the second sealant component.

16 Claims, 7 Drawing Sheets

SYSTEM AND METHOD FOR DETECTION AND REPAIR OF PULMONARY AIR LEAKS

FIELD OF INVENTION

This invention relates to the detection and repair of pulmonary air leaks.

BACKGROUND OF THE INVENTION

Persistent air leaks after lung surgery such as thoracentesis, lung biopsy or intercostal analgesic rib blocks are serious complications that result in increased morbidity and mortality as well as dramatically increased length of hospital stay. Air leaks can also occur spontaneously in a number of diseases. Most spontaneous air leaks result from rupture of blebs located at the apex of the lung. Air leaks following pulmonary procedures usually are due to incomplete apposition of the pulmonary parenchyma following resection. Fifteen percent of all patients undergoing pulmonary procedures develop air leaks and some studies have shown a prevalence as high as fifty-eight percent following lobectomy. Persistent air leaks, which are those that fail to resolve within one week, are the most frequent complication in patients undergoing general thoracic procedures.

A prolonged air leak can result in a broncho-pleural fistula—a nonhealing, abnormal communication between the lung and the chest cavity. Such fistulae may require drastic measures such as a thoracotomy with removal or repair of the affected lung and, possibly, placement of muscle or omental flaps into the chest cavity.

The patients who are predisposed to these problems, either spontaneously or iatrogenically, frequently have underlying medical problems (especially pulmonary) that make aggressive intervention a hazardous proposition. Prolonged air leaks can even result in patient death. Air leaks are the most frequent cause of extended hospital stay after thoracic surgery and results in significantly increased patient morbidity and hospital costs.

Detecting the location of an air leak is in and of itself a difficult problem. Current methods of diagnosis include high resolution cat scans, MRI's, and bronchoscopy for direct visualization of proximal airway leaks and bronchopleural fistulas. These modalities offer varying levels of reliability and satisfaction but are not consistently sensitive and accurate. The most definitive means to identify an air leak is through the relatively crude technique of open thoracotomy, in which the chest cavity is opened and filled with saline solution and then, following positive pressure ventilation, the location of bubble formation points to the area of leakage.

The current approach to repair of air leaks, once located, is to place a chest tube, if not already present, in the chest cavity with the leaking lung. If air is leaking from the lung after pulmonary surgery, chest tubes that are in place at the time of surgery can be used for this purpose. A conservative trial of applying suction to the intrathoracic tube to keep the lung expanded is the first maneuver. Occasionally, patients are discharged from the hospital with a one way "Heimlich" valve attached to the tube. This valve allows air leaking from the lung to escape from the chest cavity but does not allow air to enter and subsequently collapse the lung.

If these conservative measures do not work, a number of approaches have been attempted. Plugging the airway from within has been attempted by using a bronchoscope to attempt to localize the part of the lung that is healing and putting something into the lung to block airflow. The most common substance is fibrin glue. This technique has the shortcoming that the leak is not easy to localize if the leak is not from a readily visualized surgical bronchial stump. Thus, instilling a bronchial occluding agent into the airway will block off airflow to a significant portion of lung tissue that may or may not be the part that is leaking. In addition, this can cause pneumonia and respiratory failure.

Other techniques to seal air leaks involve approaching the leak from outside the lung. This, obviously, requires a major chest operation to mobilize and visualize the leak. The procedure is similar to finding a leak in a tire. The chest cavity is filled with saline, the lung is inflated and a search is initiated to localize the source of bubbles. Unlike a tire, however, the lung is a complexly shaped organ and it is frequently difficult, even with a major operation, to localize all leak sites. Once localized, the leaking area can be oversewn, stapled, resected or buttressed, as previously mentioned, with muscle flaps or omentum.

Recently, products have been introduced that act as sealants on the surface of the lung. These products are primarily used at the time of a pulmonary resection. The aim is to decrease the length of time that air leaks from areas of dissection or staple lines. Again, fibrin glue or other bioabsorbable sealants are applied and set on the lung surface intraoperatively. These products can only be applied to the outside of the lung in the setting of a major operation where the patient is under general anesthesia with selective lung ventilation.

Thus, a need exists for a minimally invasive system and method to detect and repair pulmonary air leaks.

BRIEF SUMMARY OF THE INVENTION

A method for repairing pulmonary air leaks is disclosed. An exemplary method comprises: introducing a first component of a biphasic sealant as a liquid into the intake air stream of the damaged lung; ensuring that there is a pressure differential between the intake air stream and the outer surface of the lung; and introducing a second component of the biphasic sealant component into the chest cavity. The first sealant component collects at the air leak site and forms a sealant in combination with the second sealant component. A system for repairing pulmonary air leaks comprises: a two-component sealant, the first part of which can be safely introduced into the damaged lung by inhalation; means for introducing the first sealant component into the damage lung by inhalation; and means for introducing the second sealant component into the chest cavity of the damaged lung.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1:
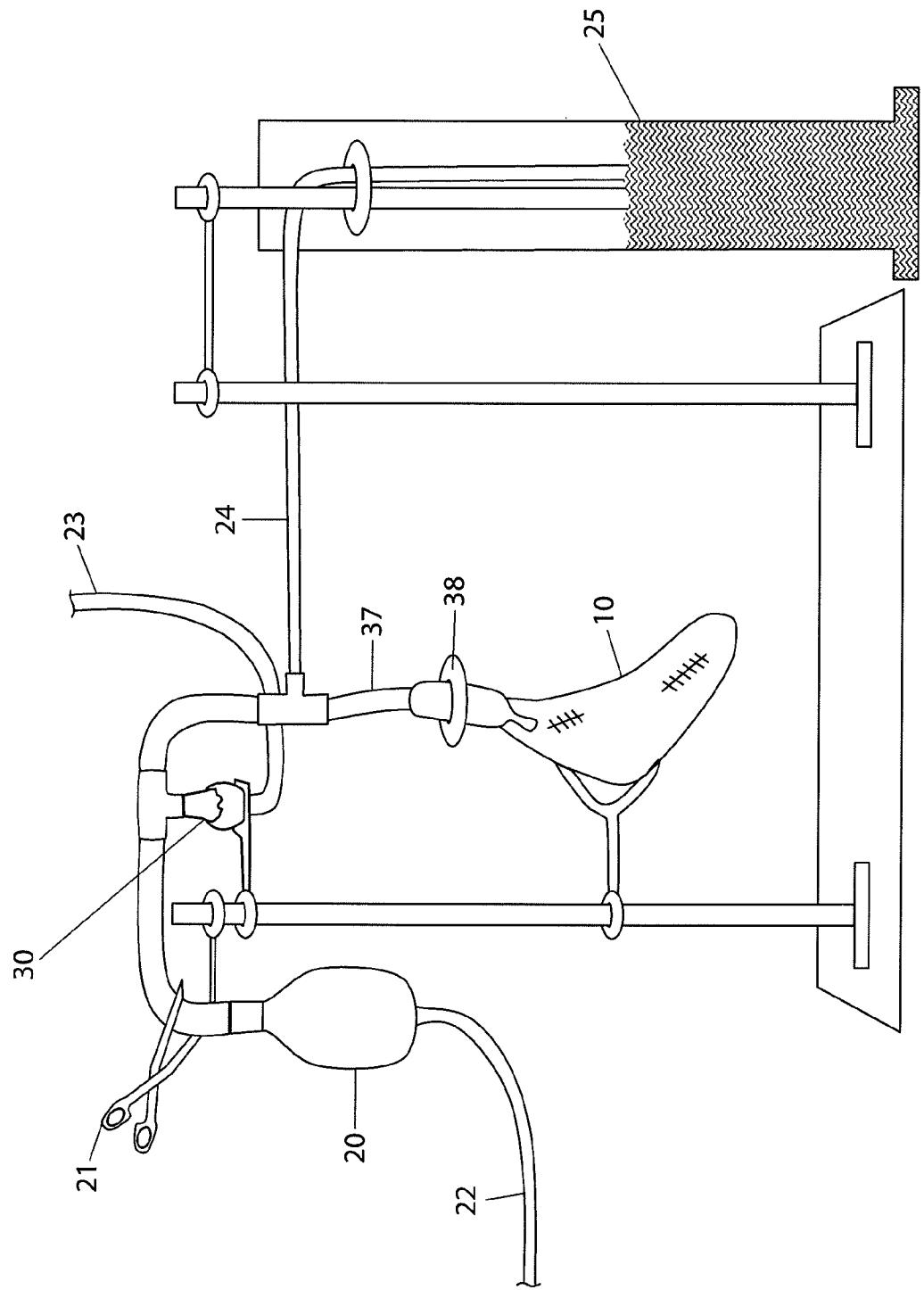
FIG. 1 is a diagram of a laboratory setup demonstrating an exemplary method for detecting a pulmonary air leak.
Figure 2:
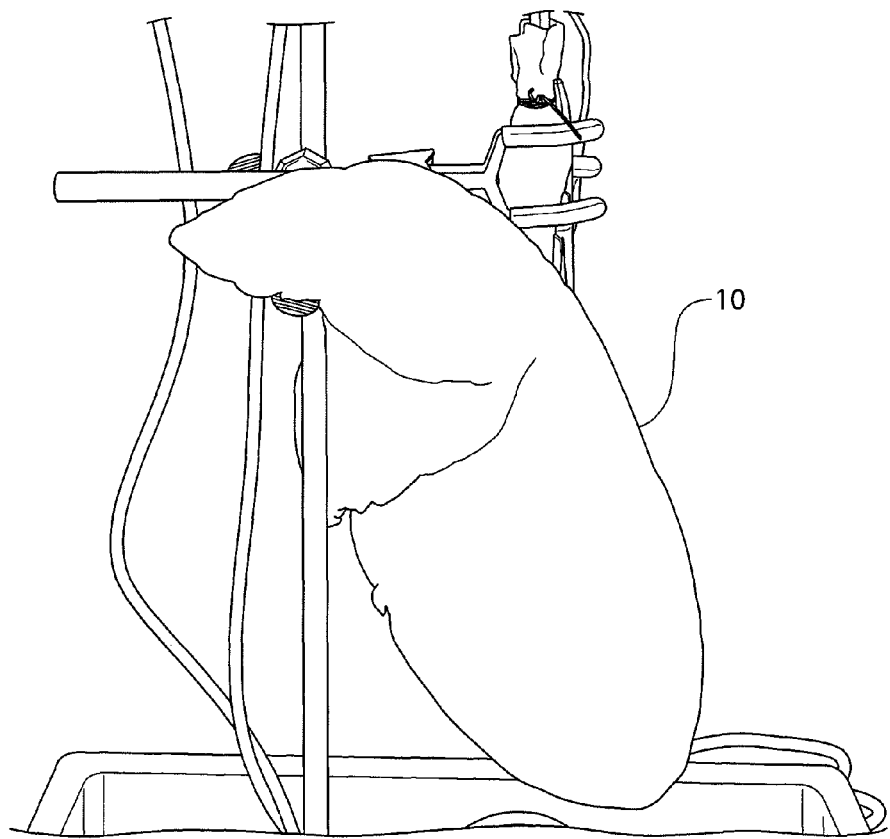
FIG. 2 is a labeled color photograph of an inflated sheep lung used in the setup of FIG. 1.
Figure 3:
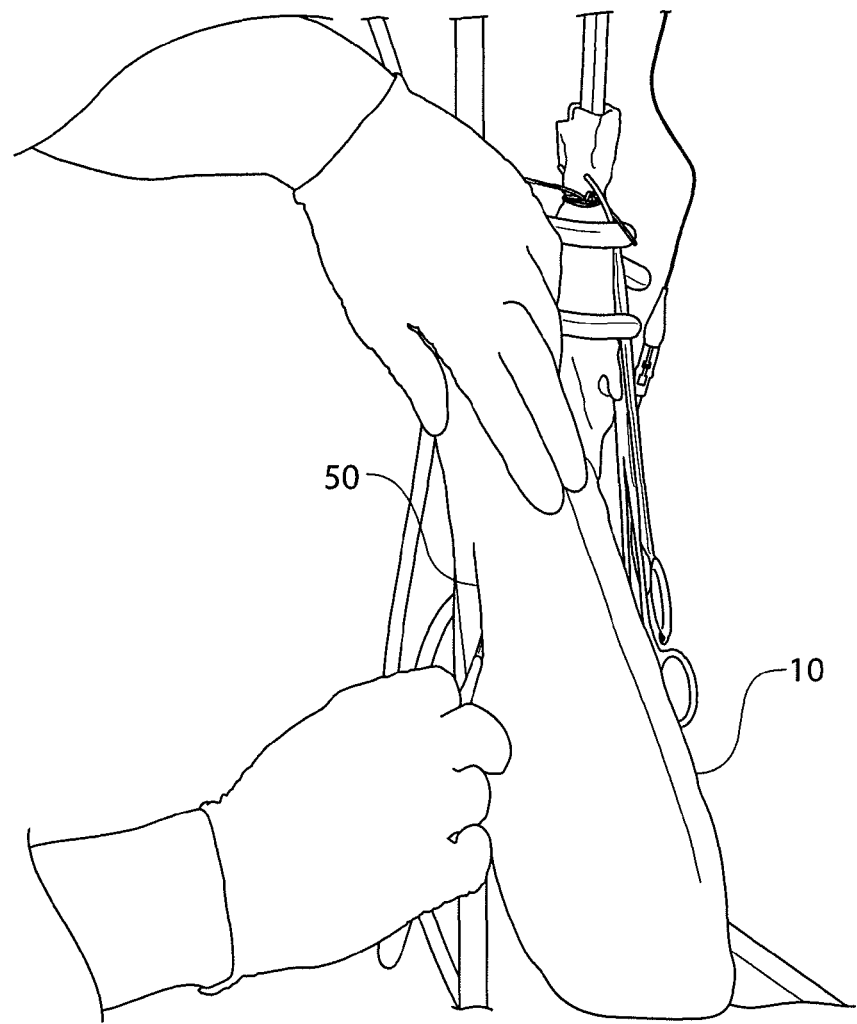
FIG. 3. is a labeled color photograph showing the creation of an air leak in the test setup of FIG. 1.
Figure 4:
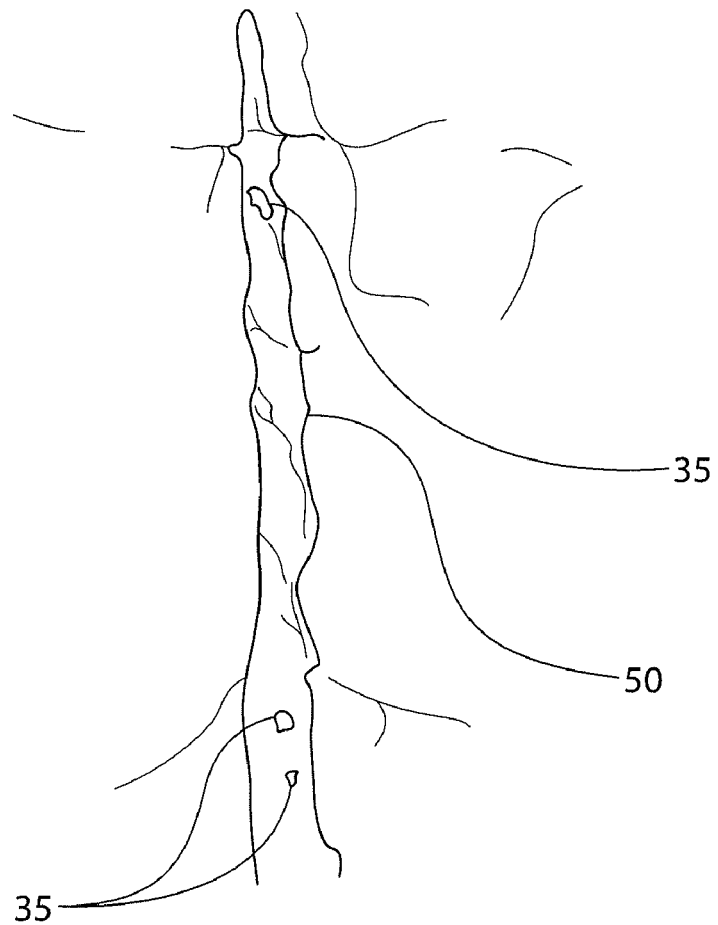
FIG. 4. is a labeled color photograph showing the state of the air leak of FIG. 3 ten seconds after the introduction of methylene blue into the air stream.

In one embodiment, a biphasic air leak sealing system is used to seal air leaks, without surgery, by importing into the lung a liquid that follows the path of the escaping gas. The liquid finds the leaks because those are the only areas with any air flow. This does not require the operator to find the leaks. The same premise is also used to find air leaks by using a tracer liquid, which also follows the path of the escaping gas.

An exemplary leak sealing system comprises two components: a prosealant and an activator. The prosealant can be a building block compound that remains liquid until cross-linked or coagulated by the activator. With a chest tube that is inserted into the patient's chest cavity on suction, the prosealant is introduced into the air stream in a nebulized form. The liquid selectively accumulates at all leak sites. Because the prosealant does not seal by itself, the lung passageways are not blocked and the sealant collects only at the site of the air leak. After a sufficient amount of prosealant has accumulated, the chest tubes are removed from suction and the activator is introduced into the chest cavity through the chest tube. This is a common practice in thoracic surgery, instilling doxycycline or talc through a chest tube for the purpose of pleurodesis. It has been well established by radionuclide studies that a liquid introduced through a chest tube is rapidly distributed throughout the chest cavity within several breaths. Wherever the activator comes in contact with the prosealant, a sealant then forms, thereby plugging the holes in the surface of the lung at exactly the correct sites.

It may not be possible in all cases for the prosealant to be aerosolized into small enough particles that can reach a leak, in which case an alternative embodiment can comprise an aerosolized activator that is introduced the air stream and a prosealant that is introduced into the chest cavity. One possible such paring comprises gelatin as the prosealant and polylactic-co-glycolic acid ("PLGA") as the activator that is introduced into the air stream. These two compounds form a well known hydro-gel reaction involving cross linking. This reaction is described in Y. Otani et al. *Biomaterials* 19 (1998) pp. 2167-2173, which is incorporated by reference herein.

In a further embodiment, the prosealant is activated by light instead of a second component.

The prosealant will have certain properties. It will be non-toxic, bioabsorbable, readily vaporized or nebulized and, likely, of low viscosity. The sealant activator and the activated sealant will also be bioabsorbable and non toxic. The ideal sealant would stretch with expansion of the lung and serve as a scaffolding for ingrowth of fibroblasts, etc, the cells responsible for the body's natural healing mechanisms. Like trying to cross a busy highway, it is suspected that the constant flow of air across a hole in the lung prevents these cells from being able to gain a foothold for sealing the leak in diseased lungs or in setting larger holes with high flow. After the body is able to scar in the hole in the lung, the ideal sealant would be absorbed by the normal mechanisms.

After the prosealant accumulates at the site of all leaks, the activator is introduced through the chest tube into the chest cavity. This bathes the lung surface in the activating agent. Wherever the prosealant and activator come in contact, the prosealant is converted into the sealant. The chest tube is then replaced to suction to evacuate any excess activator and to re-expand the lung. An exemplary activator would be non-toxic, have low viscosity and be bioabsorbable.

It is also possible that the components of fibrin glue could be used as a prosealant and activator.

In a still further embodiment, a hydroscopic single component sealant can be inhaled into the air stream. The sealant would expand upon exposure to moisture at the site of the injury. Because the lung has moisture everywhere, a liposome-type preparation could be used that shields the sealant particles from absorbing moisture for a period of time until a sufficient number of particles has begun to fill up the opening. The single component sealant would have to be bioabsorbable, nontoxic and swell in the presence of water. The particle size would have to be such that the sealant could capitalize on the selective flow phenomenon disclosed herein.

An exemplary method for leak detection and a demonstration that a liquid introduced into the lungs in a nebulized form will accumulate only at a leak site is shown in FIGS. 1-7.

FIG. 1 shows a test set up wherein an ex vivo sheep lung 10 is connected to a circuit that includes an ambu bag 20 and a nebulizer 30. Air is flowed into the nebulizer 30 from air hose 23 and into the ambu bag 20 from air hose 22. Air hoses 22 and 23 are connected to an air source (not shown). When clamp 21 is released, the ambu bag 20 is used to cycle the inflation of the lung. A pressure release tube 24 is submersed under 20 cm of water 25 to regulate air pressure into the lung 10. The nebulizer 30 is filled with methylene blue. The nebulized mist introduced into the lung is such that without the lung attached, the mist does not accumulate in any significant way. This is demonstrated by the fact that without the lung attached to an endotracheal tube 37 from the nebulizer 30, the mist emerging from the tube leaves barely a trace of blue tint on a white paper (not shown) held near the output from the tube 37.

In order for the particles of an aerosolized liquid to be diagnostically useful, they must, at a minimum, be small enough to travel throughout the bronchopulmonary tree and to the sites of parenchymal injury. Nebulized methylene blue particles are approximately between 0.4 and 2.1 microns in diameter, which makes them small enough to travel to the terminal alveoli of the human lung. In addition, it is suspected that other properties of the liquid are relevant to the ability to perform as methylene blue does in the example described herein. These properties include: the degree to which the compound is hydrophyillic or hydrophobic, distensiblity, specific weight and electrical charge.

Methylene blue is a widely used aromatic chemical compound. It is a solid, dark green odorless powder that yields a blue solution when dissolved in water. Due to its reducing agent properties, it is employed as a medication for the treatment of methemoglobinemia and cyanide toxicity. It is also used as a dye and staining agent in multiple surgical arenas, including the identification of sentinel lymph nodes in breast cancer, melanoma, and lung cancer. It is also being used for the localization of pulmonary nodules in adult and pediatric patients.

FIG. 2 shows the lung 10 completely inflated and the fact that there is no trace of the methylene blue on the lung surface. When a small puncture wound is created through which air can be heard to escape, within 5-10 seconds, the hole becomes blue and grows progressively darker with further ventilation. FIG. 3 shows the creation of a 5 cm incision, approximately 0.5 cm in depth on the surface of the lung. With the lung inflated and the aerosolized methylene blue introduced into the air stream, the incision 50 immediately turns blue and within a minute is weeping blue fluid. FIG. 4 shows the incision 50 ten seconds after being made, with blue dots of methylene blue 35 already appearing on the lung surface.

Figure 5:
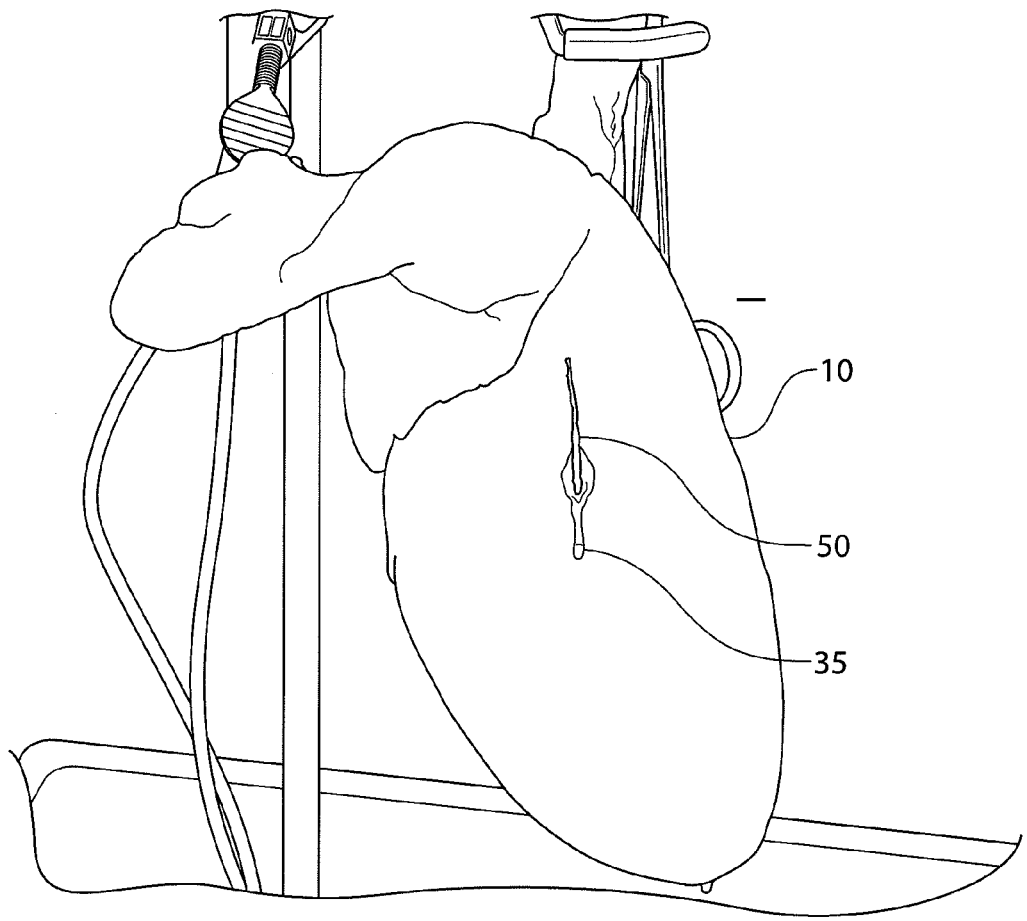
FIG. 5. is a labeled color photograph showing the state of the air leak of FIG. 3 one minute after the introduction of methylene blue into the air stream.

FIG. 5 shows the incision 50, one minute after being made, with the methylene blue 35 dripping at the base of the opening.

Figure 6:
FIG. 6 is a labeled color photograph showing the location of the methylene blue after the deepening of the incision shown in FIG. 3.
Figure 7:
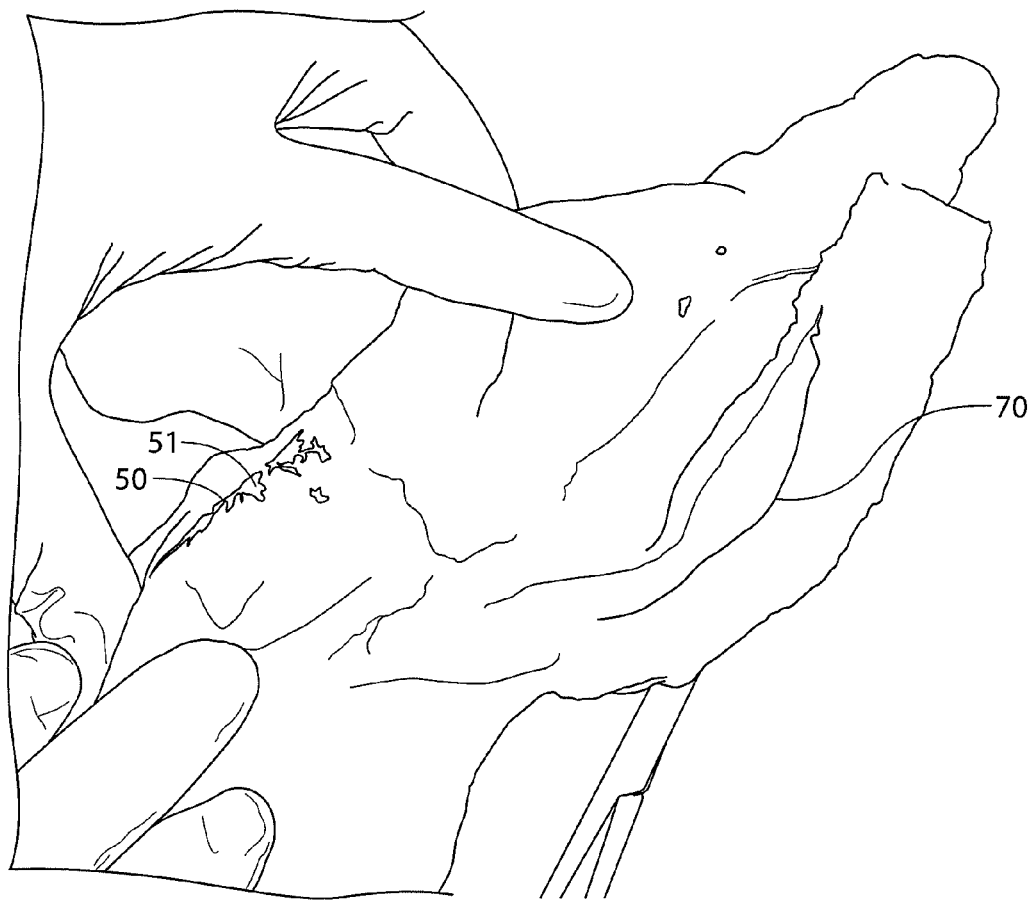
FIG. 7 is a labeled color photograph showing the lung of the preceding figures further dissected.

FIG. 6 shows the incision 50 opened up for examination. Unexpectedly, the entire incision is pink, with no evidence of methylene blue except at the site of the incision 50 and approximately 1 mm of tissue surrounding it. FIG. 7 shows the lung 10 opened, starting in the trachea 70 and extending out along the major airways. This reveals methylene blue only at the incison 50 and a short distance into the airways leading to the incision. The rest of the lung is without significant evidence of the methylene blue.

The method for accumulating a liquid at a pulmonary leak point as demonstrated in FIGS. 1-7 wherein an ex vivo lung is inflated with positive pressure is no different from a physical standpoint from exposing an in vivo lung to negative pressure via a chest tube that is on suction. In either case there is a pressure gradient directing flow through leaks and it is believed that there is more or less static air in the non-leaking air sacs, which, it is believed, does not allow nebulized liquid to accumulate in those areas.

The advantages of the system described herein over every other system currently in use are significant. The system finds the leaks by itself. There is no need for bronchoscopy or surgery, both of which are minimally or partially successful at best for locating all sites of leakage in many situations. Allowing the leaks to determine where the prosealant accumulates is really the only way to localize all leaks. The procedure can be performed at the bedside with the patient awake—no need to travel to the operating room or a bronchoscopy suite. Lastly, once the procedure is commercialized, it could be performed by any physician and would be the procedure of choice for any patient with an air leak from any cause. Any such patient would already have a chest tube in place and that would represent the only procedural part of the biphasic sealant system.

While the invention has been described in detail and with reference to specific examples thereof, it will be apparent to one skilled in the art that various changes and modifications can be made therein without departing from the spirit and scope thereof.

What is claimed is:

1. A method for repairing pulmonary air leaks in a lung residing in a chest cavity of a patient in need thereof and having an intake air stream and an outer surface of the lung comprising:
   introducing a first biphasic sealant component as a liquid, an aerosol, or a particulate stream into the intake air stream;
   ensuring that there is a pressure differential between the intake air stream and the outer surface of the lung by exposing the lung to negative pressure via a chest tube that is on suction;
   introducing a second biphasic sealant component into the chest cavity, whereby the second biphasic sealant component upon contact with the first sealant component forms a sealant.

2. The method of claim 1, wherein the first biphasic sealant component is nebulized and has a particle size of approximately 1 micron.

3. The method of claim 1, wherein the first and second biphasic sealant components form fibrin glue when combined.

4. The method of claim 1, wherein the first biphasic sealant is PLGA and the second biphasic sealant is gelatin.

5. The method of claim 1, wherein said second biphasic sealant component is introduced into the chest cavity by a tube.

6. The method of claim 1, wherein the first and second biphasic sealant components form a bioabsorbable sealant when combined.

7. The method of claim 1, wherein the first and second biphasic sealant components form a biocompatible sealant when combined.

8. A system for repairing pulmonary air leaks in a lung residing in a chest cavity of a patient in need thereof and having an intake air stream and an outer surface of the lung comprising:
   a selectively curable sealant capable of being introduced into the lung by inhalation;
   means for introducing the sealant as a liquid, an aerosol, or a particulate stream into the lung by inhalation;
   and a chest tube that is on suction for ensuring a pressure differential between the intake air stream and the outer surface of the lung.

9. The system of claim 8 wherein the selectively curable sealant is a biphasic sealant and further comprising:
   a second sealant component; and
   means for introducing said second sealant component to the outer surface of the lung.

10. The system of claim 9 wherein the selectively curable sealant has a particle size of approximately 1 micron.

11. The system of claim 9 wherein said means for introducing said second sealant component include a tube inserted into the chest cavity.

12. The system of claim 8 wherein said selectively curable sealant is cured by light and further comprising:
   means for introducing light to the outer surface of the lung.

13. A system for repairing pulmonary air leaks in a lung residing in a chest cavity of a patient in need thereof and having an intake air stream and an outer surface of the lung comprising:
   a first biphasic sealant component introduced as a liquid, an aerosol, or a particulate stream into the intake air stream;
   a second biphasic sealant component introduced into the chest cavity, which forms a sealant when combined with the first sealant component;
   and a chest tube that is on suction for ensuring a pressure differential between the intake air stream and the outer surface of the lung.

14. The system of claim 13 wherein the first biphasic sealant component is PLGA and the second biphasic sealant component is gelatin.

15. The system of claim 13, wherein the first and second biphasic sealant components form a bioabsorbable sealant when combined.

16. The system of claim 13, wherein the first and second biphasic sealant components form a biocompatible sealant when combined.

* * * * *